(12) United States Patent
Pereira et al.

(10) Patent No.: US 12,050,159 B2
(45) Date of Patent: Jul. 30, 2024

(54) EMBOSSED FILM BIOPROCESSING CONTAINERS AND INTEGRITY TESTING OF BIOPROCESSING CONTAINERS

(71) Applicant: EMD Millipore Corporation, Burlington, MA (US)

(72) Inventors: Brian Pereira, Woburn, MA (US); Stephen Proulx, Boxborough, MA (US)

(73) Assignee: EMD Millipore Corporation, Burlington, MA (US)

( * ) Notice: Subject to any disclaimer, the term of this patent is extended or adjusted under 35 U.S.C. 154(b) by 51 days.

(21) Appl. No.: 16/644,109

(22) PCT Filed: Sep. 27, 2018

(86) PCT No.: PCT/US2018/053109
§ 371 (c)(1),
(2) Date: Mar. 3, 2020

(87) PCT Pub. No.: WO2019/070502
PCT Pub. Date: Apr. 11, 2019

(65) Prior Publication Data
US 2020/0209098 A1   Jul. 2, 2020

Related U.S. Application Data

(60) Provisional application No. 62/567,266, filed on Oct. 3, 2017.

(51) Int. Cl.
*G01M 3/32* (2006.01)
*B01L 3/00* (2006.01)

(52) U.S. Cl.
CPC .......... *G01M 3/3218* (2013.01); *B01L 3/505* (2013.01); *B01L 2300/0861* (2013.01)

(58) Field of Classification Search
CPC .......... G01M 3/26; G01M 3/3218; A61J 1/10; B01L 3/505; B01L 2300/0861
See application file for complete search history.

(56) References Cited

U.S. PATENT DOCUMENTS 4,790,815 A * 12/1988 Balteau ............... A61M 1/1668
604/408
4,858,463 A * 8/1989 Rosse .................. G01M 3/329
73/49.3

(Continued)

FOREIGN PATENT DOCUMENTS

CN      1211222 A     3/1999
CN    103029892 A     4/2013

(Continued)

OTHER PUBLICATIONS

International Search Report received for PCT Patent Application No. PCT/US2018/053109, mailed on Dec. 19, 2018, 4 pages.

(Continued)

*Primary Examiner* — Natalie Huls
(74) *Attorney, Agent, or Firm* — EMD Millipore Corporation

(57) ABSTRACT

A testing method that includes the steps of evacuating air from a container to a negative atmospheric pressure, the container being a collapsible, flexible container, and comprising at least two opposing flexible walls, wherein a surface of at least one of the walls internal to the container comprises a plurality of channels or recessed features on said at least one wall and monitoring a mass flow or a state of vacuum so as to determine the integrity of the container. The container can be of any size or conformation, with or without attached fittings.

13 Claims, 7 Drawing Sheets

(56) References Cited

U.S. PATENT DOCUMENTS

| | | | | |
|---|---|---|---|---|
| 5,578,028 | A | * | 11/1996 | Drago ............... A61M 1/02 604/408 |
| 5,728,086 | A | * | 3/1998 | Niedospial, Jr. ...... A61J 1/1487 604/408 |
| 6,179,822 | B1 | * | 1/2001 | Niedospial, Jr. .......... A61J 1/10 604/408 |
| 6,179,823 | B1 | * | 1/2001 | Niedospial, Jr. .......... A61J 1/10 604/408 |
| 11,262,268 | B2 | * | 3/2022 | Wurm ................. G01M 3/02 |
| 2003/0219177 | A1 | | 11/2003 | Salvaro |
| 2011/0011164 | A1 | * | 1/2011 | Terentiev ............ G01M 3/229 73/40.7 |
| 2017/0205307 | A1 | * | 7/2017 | Hogreve ............. G01M 3/229 |
| 2018/0087997 | A1 | * | 3/2018 | Thenard .................. A61J 1/18 |
| 2019/0046397 | A1 | * | 2/2019 | Harhen ................ B01D 69/10 |
| 2019/0285508 | A1 | * | 9/2019 | Mathe .................. G01M 99/00 |
| 2022/0260449 | A1 | * | 8/2022 | Thenard ............. G01M 3/3281 |

FOREIGN PATENT DOCUMENTS

| | | | |
|---|---|---|---|
| CN | 104743222 | A | 7/2015 |
| CN | 105636870 | A | 6/2016 |
| CN | 106802220 | A * | 6/2017 |
| DE | 2421433 | A1 | 11/1975 |
| EP | 0216327 | B1 | 10/1990 |
| EP | 0420519 | A1 | 4/1991 |
| JP | 56-100336 | A | 8/1981 |
| JP | 60-246757 | A | 12/1985 |
| JP | 62-201154 | A | 9/1987 |
| JP | 1-230360 | A | 9/1989 |
| JP | 3-261477 | A | 11/1991 |
| JP | 6940697 | B2 | 9/2021 |
| WO | 97/29020 | A1 | 8/1997 |
| WO | 02/066227 | A1 | 8/2002 |
| WO | 02/074522 | A1 | 9/2002 |
| WO | 03/039983 | A1 | 5/2003 |
| WO | 2005/016774 | A1 | 2/2005 |
| WO | 2005/058699 | A2 | 6/2005 |
| WO | 2006/036275 | A2 | 4/2006 |
| WO | 2008/131670 | A1 | 11/2008 |
| WO | 2017/145703 | A1 | 8/2017 |
| WO | 2019/070502 | A1 | 4/2019 |

OTHER PUBLICATIONS

Extended European Search Report received for European Patent Application No. 21192523.5 mailed on Jan. 10, 2022, 7 pages.

Office Action received for Chinese Patent Application No. 201880064547.4 mailing date Feb. 2, 2024, 4 pages (1 Page of English translation & 3 Pages of official copy).

Extended European Search Report received for European Patent Application No. 23189863.6 mailing date Nov. 30, 2023, 7 pages.

Office Action received for Chinese Patent Application No. 201880064547.4 mailing date Sep. 29, 2023, 4 Pages (1 Page of English translation & 3 Pages of official copy).

Office Action received for Chinese Patent Application No. 201880064547.4 mailing date Feb. 27, 2023, 15 (7 Pages of English translation & 8 Pages of official copy).

* cited by examiner

EMBOSSED FILM BIOPROCESSING CONTAINERS AND INTEGRITY TESTING OF BIOPROCESSING CONTAINERS

RELATED APPLICATIONS

The present application is a US National Stage application of International Application No. PCT/US2018/053109, filed Sep. 27, 2018, which claims the benefit of priority of U.S. Provisional Patent Application No. 62/567,266, filed date Oct. 3, 2017, the entire content of each of which is incorporated herein in its entirety.

BACKGROUND

Field of the Technology

Provided herein are materials useful for manufacturing bioprocessing container(s) and methods of integrity testing bioprocessing containers. Film materials having textured or embossed patterns, for manufacturing disposable, single-use containers and systems useful for containing, transporting, mixing and/or processing biological liquids and/or solutions, are disclosed. More particularly, integrity testing of such containers, including small and large volume containers of varying dimensions and complexity, are disclosed.

Description of the Related Art

Fluids used in industries, such as bioprocessing and pharmaceutical fields, have been traditionally processed in systems that use stainless steel containers. After each use, these stainless-steel containers are disassembled, cleaned, sterilized and reassembled before reuse to provide sterile components. The cleaning and sterilization procedures are time-consuming, expensive and cumbersome. If the containers are not properly cleaned, reassembled, and sterilized, the containers can be contaminated and compromise the fluid contents in a subsequent use. Furthermore, the cleaned and sterilized containers typically need to be validated before use, adding expense and time burden to the process.

To provide greater flexibility in processing and to reduce time spent on validating equipment, manufacturers have developed disposable pre-sterilized or on-site sterilizable containers that are used once and disposed. Flexible or collapsible bags are an example of such single-use, disposable containers. Various attachments on the single-use containers, such as tubing, port fittings, connectors, mixing elements and the like, may also be disposed with the container.

Maintaining sterility of the single-use container or bag is of vital importance, particularly for the food, beverage, and pharmaceutical industries. Contamination poses serious health and environmental risks. Furthermore, loss of product through leaks can cause significant economic loss.

Stainless steel containers are robust and are not readily punctured or torn. In contrast, flexible containers, which can be made from plastic or silicone materials, are more susceptible to being torn or punctured. Therefore, the integrity of flexible containers is tested to check for defects that would compromise the system.

Major integrity failures in single-use bioprocessing containers are often readily apparent and can be identified visually. Integrity failures include seam failures, rips, and/or visible puncture holes within the container or film(s) of which the container is manufactured. However, smaller defects, such as microscopic holes or tears, cannot be detected by mere visual inspection. These smaller defects represent a greater risk since, in addition to leaking, they can permit the passage of microorganisms, particles, fluids or other unwanted materials into the system, which may go undetected for a period of time during use. Discovering contamination after a bioprocessing run has started mandates that the batch be discarded, and the process started again, which wastes time and resources.

Current methods of non-destructive integrity testing inflate the bioprocessing containers, such as bags, with a gas and test for leak of that gas. Leaks can be measured in different ways. For example, in the pressure decay integrity test, the bag is inflated with air to a set pressure, stabilized for a predetermined time to counteract stretching and adiabatic effects of filling, and monitored for decay in the pressure in the bag. Loss of pressure indicates a leak.

The pressure decay integrity test is relatively reliable for small containers, but not for larger containers. Increasing pressure in a larger flexible container during a pressure decay test subjects the container to much greater strain on the material than for smaller containers and is more susceptible to burst. This is because the hoop stress in the wall of the container increases with the radius. Therefore, a larger container that has the same wall thickness as a smaller bag is subject to greater stress under the same pressure.

For example, a 2-liter flexible film single-use process container (for example, MOBIUS® PureFlex™ bags, manufactured by MilliporeSigma, Burlington, Mass., USA) can be safely inflated to 1.5 pounds per square inch (PSI) (10.3 kPa). At this pressure, a hoop stress of roughly 300 PSI (2068 kPa) will be developed in the wall of the bag. This is acceptably below the 1360 PSI (9377 kPa) yield stress of the film and, therefore, will not damage the bag. At these conditions, with a sensitive pressure transducer, a 30 µm defect can be found within 5 minutes. However, sensitivity is lost significantly with increasing size of the container. For example, if the container or bag has a 20-liter volume, a test pressure of 1.5 PSI (34.5 kPa) develops a hoop stress of 1500 PSI (10342 kPa), which typically exceeds the yield stress of the film. For a 20-liter sized bag, the test pressure would have to be reduced to 0.6 PSI (4.1 kPa) to keep the hoop stress well below the yield stress. At this lower test pressure and higher bag volume, only larger defects of at least 170 µm are expected to be identified in 5 minutes. In other words, as the container or bag volume increases, the test pressure needs to decrease and, therefore, the test sensitivity, unfavorably, decreases commensurately.

Another problem with using pressure decay methods to test bags is that the flexible nature of disposable containers permits expansion of the film material itself, which in turn appears as pressure decay, leading to a false reading of an integrity failure. The presence of an actual defect in a large, flexible container can also be missed during a pressure decay test because the difference in pressure decay caused by the leak is masked by the pressure decay caused by the stretching of the film material, and/or the seams of the film materials, itself.

Past attempts to minimize the film material stretch of large flexible containers in the pressure decay test, thereby reducing the hoop stress effect, include methods wherein the integrity test is conducted with the container restrained between two rigid plates. While this reduces the amount of material stretch during the pressure decay test, this test suffers from masking defects located adjacent to the rigid plates, i.e., the plates seal the defects. Consequently, the problem remains that a defective container may erroneously pass the integrity test.

To avoid the problem of restraining plates masking actual defects, an additional porous material needs to be placed adjacent to the plates. The porous material acts to prevent defects from being sealed off against the plate. This is, however, unsuitable for containers that are not sufficiently flat. For example, the pressure decay test of large bioprocessing containers with attached fittings, such as tubing, connectors, etc., is not suitable for use with constraining plates. The attached fittings compromise the ability of the rigid plates to lie flush with the container, thereby defeating the purpose of the plates, e.g., to minimize material stretch during pressurization. Additionally, disproportionate pressure may also be exerted at points of contact between the constraining plates and fittings on the container, which may, in turn, cause the rupture of a join or seal between the fitting and the container.

Other integrity testing methods have included the use of Helium gas. In this test, the container being tested is connected to a Helium source and placed into a sealed, rigid vessel with an outlet. The air is pulled from the rigid vessel through the outlet, and Helium gas is injected into the container being tested. If the container has a defect, Helium escapes from the container into the rigid vessel and can be detected using mass spectroscopy. However, volumetric leak flow rate depends on gas viscosity, and Helium has a higher gas viscosity than a gas such as Nitrogen. Consequently, a container with a defect will leak less with Helium than Nitrogen under the same differential pressure. As such, leaks can take longer to detect or require higher pressures to detect. Furthermore, Helium can diffuse through many materials, including silicone which is often used in flexible bioprocessing containers. Consequently, detecting Helium in the test may be the result of a defect, or, alternatively, a false positive from Helium diffusion through the film material itself.

In view of the foregoing, an integrity test that overcomes the above deficiencies would represent an advance in the art.

SUMMARY

A testing method that includes the steps of evacuating air from a container to a negative atmospheric pressure, the container being a collapsible, flexible container, and comprising at least two opposing flexible walls, wherein a surface of at least one of the walls internal to the container comprises a plurality of channels on said at least one wall and monitoring mass flow so as to determine the integrity of the container. The container can be of any size or conformation, with or without attached fittings.

Integrity tests according to embodiments of the present disclosure are highly sensitive, sensitive enough to detect microscopic defects in any size or conformation of vessel, whether a single-use disposable two-dimensional (2-D) or three-dimensional (3-D) bag, with or without attached fittings. Some embodiments disclosed herein comprise methods for determining the integrity of a collapsible, flexible bioprocessing container that eliminates variation in testing due to stretching of materials and films during testing. Some embodiments disclosed herein comprise methods for determining the integrity of a collapsible, flexible bioprocessing container that eliminates the creation of defects due to stretching of materials and films during testing A highly sensitive and rapid method of determining the integrity of a collapsible, flexible bioprocessing container is disclosed. The method includes evacuating air from the container to a negative atmospheric pressure, the container being a collapsible, flexible bioprocessing container, and comprising at least two opposing flexible walls, wherein the surface of the walls internal to the container comprise a plurality of channels on said walls and; monitoring mass flow so as to determine the integrity of the container. The bioprocessing container can be of any size or conformation, with or without attached fittings. In some embodiments, the container comprises at least two opposing flexible walls. The surface of at least one wall, one of two opposing walls, or all the walls, that are internal to the container comprise a plurality of channels. In some embodiments, the plurality of channels is embossed on the wall(s). Alternatively, or additionally, the internal surface of the wall(s) is a matte surface. In some embodiments, the collapsible, flexible bioprocessing container is pre-folded. Any embodiment according to the disclosure contemplates a container further comprising fittings, tubing, connectors, or any combination thereof.

In some embodiments, an integrity test comprises evacuating air from the container to a negative atmospheric pressure and monitoring a mass flow of air or a vacuum decay, so as to determine the integrity of the container. An increase in mass flow during monitoring indicates the presence of a leak.

In some embodiments, a method of detecting a 2 micron or larger defect in a collapsible, flexible bioprocessing container is disclosed. The method comprises providing a collapsible, flexible bioprocessing container, which container comprises at least two opposing flexible walls. The surface of at least one wall, one of two opposing walls, or all the walls, that are internal to the container and further comprises a plurality of channels. The method comprises evacuating air from the container to a negative atmospheric pressure and monitoring mass flow of air or vacuum decay. An increase in mass flow and/or a loss in the vacuum indicates the presence of a defect in the container.

In some embodiments, the integrity test comprises evacuating air to a negative atmospheric pressure between approximately −1 (negative) PSI (6.9 kPa) to approximately −14 (negative) PSI (96.5 kPa).

BRIEF DESCRIPTION OF THE DRAWINGS

The drawings are provided to illustrate one or more embodiments of the disclosure and are not to be construed as limiting the scope of the claims.

DETAILED DESCRIPTION

Figure 1A:
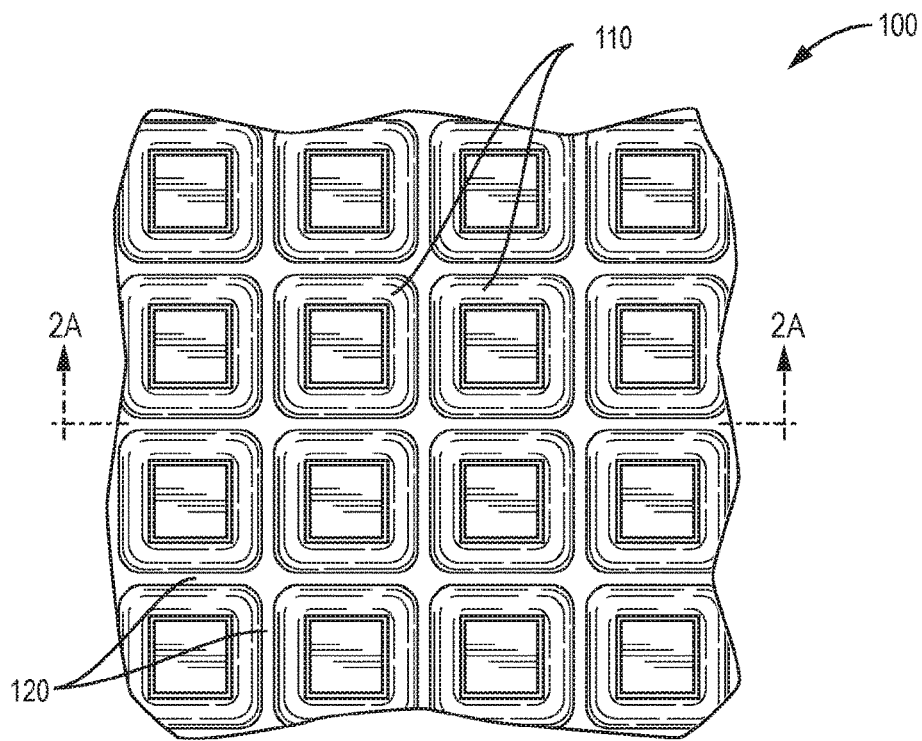
FIG. 1A depicts a textured or embossed pattern having raised features and recessed channels on an interior of a flexible film according to embodiments of the disclosure.

Traditional pressure-based integrity tests have limitations, especially as the volume of the flexible container increases in size (e.g., more than 20 liters) and in complexity (e.g., 3-D versus 2-D, containers with, optionally, attached ports, connectors, tubing, and other fittings). It is to be understood that the terms containers and bags are used interchangeably throughout this disclosure.

Contrary to the traditional integrity tests that need to inflate the container with or without a tracer gas, the present system uses a vacuum to test the integrity of a flexible container. The presence or measurement of fluid flow, e.g., air or another gas, following the evacuation of the flexible container indicates the presence of a defect. Similarly, the measurement of a loss of vacuum would also indicate the presence of a defect, i.e., vacuum decay.

Embodiments of the vacuum integrity test(s) disclosed herein are unexpectedly more sensitive than traditional tests that inflate the containers. Furthermore, some embodiments of the vacuum integrity test(s) disclosed herein can detect a defect(s) more rapidly than pressure decay tests. The vacuum integrity test(s) disclosed herein avoid stretching of the film material under the inflation pressure, thereby avoiding any risk of rupture or creation of other defect(s).

After traditional inflation-based integrity tests, the container needs to be deflated and prepared for packaging and shipping. Unfortunately, this handling process can inadvertently introduce defects in the flexible container through improper handling, abrasion, creasing, and/or folding. Conveniently, the vacuum integrity test according to embodiments of the disclosure can be performed on bioprocessing containers and systems that are already folded and ready for final packaging and shipping. This method(s), therefore, avoids introducing the defects caused during handling of the container after traditional tests. Also, final packaging and shipping can be performed following, e.g., immediately, successful testing, saving time, logistical considerations, expenses, and like operational concerns.

The vacuum integrity test(s) disclosed herein is also faster than traditional inflation-based integrity tests, which facilitates faster quality control and higher output for manufacturers and faster validation by end-users.

Embodiments of the vacuum integrity test(s) disclosed herein uses a vacuum to evacuate air from the interior of a flexible container having the specific properties described herein. Once the container is sufficiently evacuated, further air flow can only be the result of a defect or leak in the bag. Similarly, once the container is sufficiently evacuated, the presence of a loss of vacuum, i.e., vacuum decay, can only be the result of a defect or leak in the bag. Using a vacuum to remove air from traditional containers having flat, non-textured walls, or non-embossed walls is not efficacious. In this situation, when vacuum is applied to a traditional container, the interior faces of the container are brought into intimate contact with each other (i.e., when the container collapses). Pockets of air cannot be fully evacuated due to the sealing effect of the collapsed walls, occurring for either 2D and/or 3D flexible containers. In this state, defects are masked, because of the intimate contact of the interior walls. A hole/defect in one wall, will be sealed against the other wall, thereby blocking any air flow through the hole/defect. Also, any defect in an air pocket behind the sealed surfaces are similarly masked. The presence of the hole/defect is, therefore, undetectable.

Some embodiments of the method disclosed herein avoid these problems via the use of a textured or embossed film in construction of the flexible container. Specifically, embodiments of the disclosure comprise bags or biocontainers wherein the interior walls of a container or bag are produced with an embossed or textured pattern. The high points, e.g., raised areas, of any pattern, such as raised squares having lowered channels therebetween, according to embodiments of the disclosure, act as spacers that maintain a small separation between the interior walls of the container when it is in its collapsed state. The space, e.g., channels thereby produced between the raised areas, prevent defects from being sealed off by the opposing interior wall of the container during vacuum testing. This small, open channel(s) allows air flow coming from a defect to occur under vacuum testing. This air flow is detected by a sensitive mass flow meter that is in-line between the flexible container being tested and a reference vacuum tank. In some embodiments, square areas are recessed into a surface of the textured or embossed film, wherein the raised areas are rails.

Figure 3:
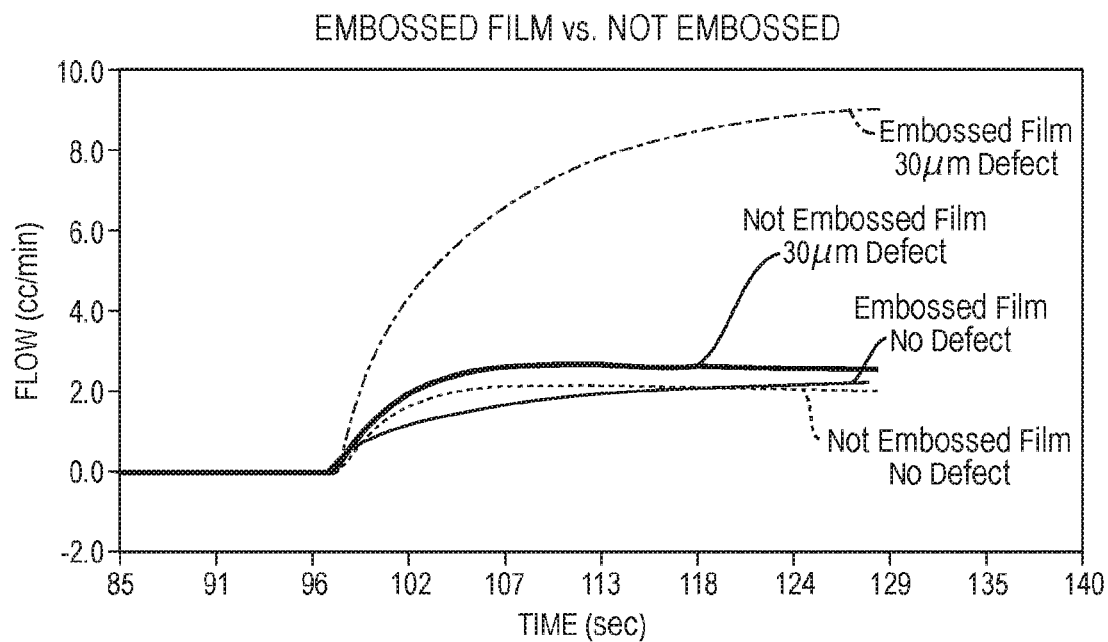
FIG. 3 is a graph comparing integrity test results with flexible containers having smooth or embossed walls, with or without an added defect.

By way of example, and not limitation, FIG. 3 shows the effect of having an embossed pattern on the interior wall of the container. A container with the embossed pattern shows a relatively high air flow when a defect is in place. In contrast, the air flow through a container without an embossed film is significantly lower. Without intending to be limited by theory, it is believed that the embossed film, which presents as peaks and valleys, prevents the film from sealing against itself, which can interfere with the identification of defects.

Optionally, the vacuum integrity test can be performed before shipping, after delivery, before use, and/or after use. In this way, the integrity of the disposable, flexible container can be assured when it leaves the manufacturing facility, upon receipt by the customer, before filling with ingredient(s) and processing, and after processing is complete. Furthermore, multiple tests can be conducted without the risk of creation of defects.

In accordance with certain embodiments, the flexible container is designed to receive, hold, mix and/or dispense materials, such as bioprocessing media, buffers, fluids, cells, tissue, and the like. Typically, the flexible container is aseptic or sterile.

The flexible container can be formed from a flexible monolayer film or multilayer film, the film forming one or more flexible walls. The flexible film can have a polymeric composition comprising one or more materials such as polyethylene, including ultrahigh molecular weight polyethylene, linear low density polyethylene, low density or medium density polyethylene; polypropylenes; ethylene vinyl acetate (EVOH); polyvinyl chloride (PVC); polyvinyl acetate (PVA); ethylene vinyl acetate copolymers (EVA copolymers); blends of various thermoplastics; co-extrusions of different thermoplastics; multilayered laminates of different thermoplastics; or the like. By "different" it is meant to include different polymer types such as polyethylene layers with one or more layers of EVOH as well as the same polymer type but of different characteristics such as molecular weight, linear or branched polymer, fillers and the like. Typically, medical grade and/or animal-free plastics are used. The film is generally sterilizable such as by steam, ethylene oxide, or radiation such as beta or gamma radiation. Most films used in the manufacture of flexible, single-use biological containers have good tensile strength, low gas transfer and are either transparent or at least translucent. Typically, the material is unsupported and/or is weldable. Also, the film used to manufacture the containers is clear or translucent, allowing visual monitoring of the contents of the container. The container is typically provided with one or more inlets, one or more outlets and one or more optional vent passages. One or more impeller assemblies can be positioned in the container for mixing the container contents.

In some embodiments, the container may be a disposable, deformable, foldable bag that defines a volume, is sterilizable for single-use, and capable of accommodating contents, such as biopharmaceutical liquids. In some embodiments, the container can accommodate one or more mixing devices partially or completely within the interior of the container. Mixing devices include but are not necessarily limited to impellers, baffles, spargers, and the like, as are known to those in the art. The volume can be a closed volume that can be opened, such as by suitable valves, to introduce a fluid into the volume, and to dispense fluid therefrom. In some embodiments, the flexible containers can include ports, connectors, tubing, baffles, vortex breakers, additional bags, and other fittings. Containers according to some embodiments disclosed herein are sometimes referred to as bioprocessing systems.

Flexible containers, such as bioprocessing bags, for this vacuum integrity test(s), disclosed herein, are not limited in size. Indeed, unlike traditional inflation-type integrity tests, this vacuum integrity test is equally suited for very large containers (e.g., at least or about 2000 liters, 3000 liters, 3500 liters, 5000 liters, or more), as well as smaller containers (e.g., 50 liters, 10 liters, 5 liters, 1 liter, or the like). Similarly, vacuum integrity test(s) described herein can be applied to flexible containers that are 2-D (e.g., pillow-shaped bags) or 3-D (cylindrical, cuboid, and/or the like, containers).

Figure 1B:
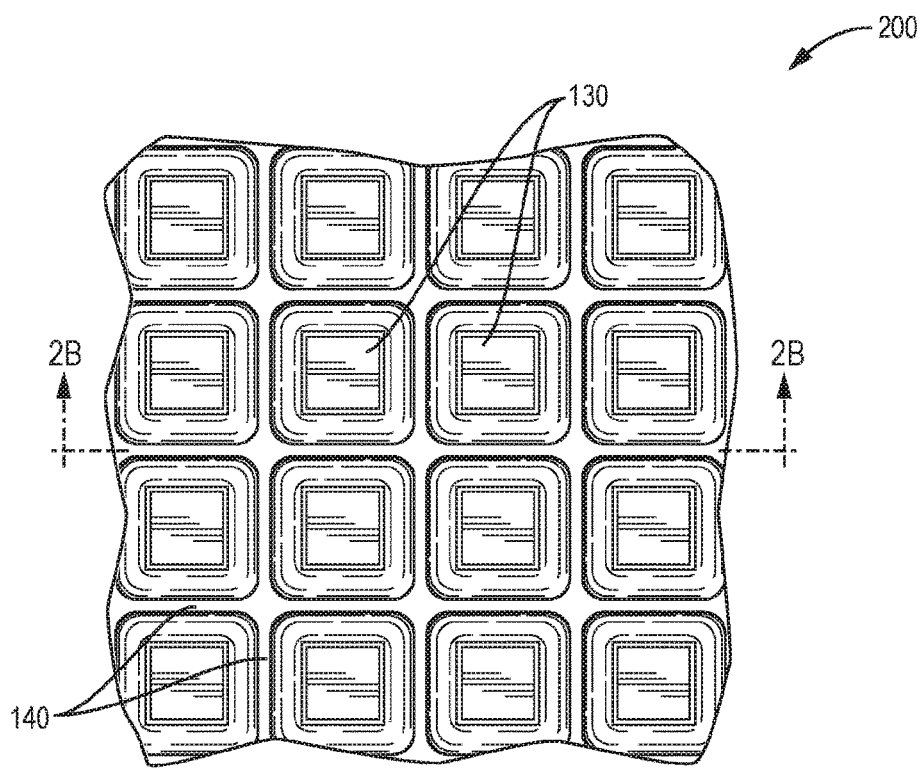
FIG. 1B depicts a textured or embossed pattern having recessed features and raised channels on an interior of a flexible film according to embodiments of the disclosure.
Figure 2A:
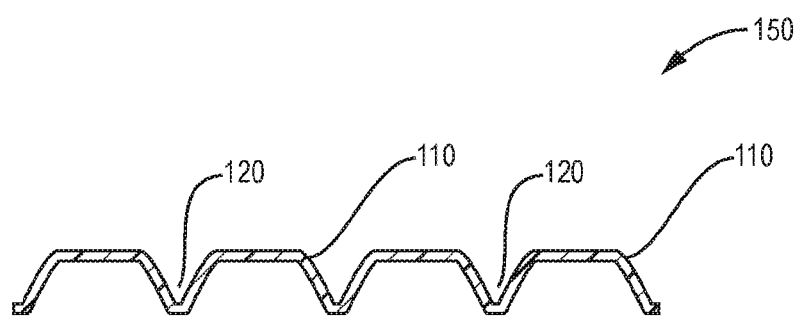
FIG. 2A depicts a cross section view of the textured or embossed pattern of FIG. 1A.
Figure 2B:
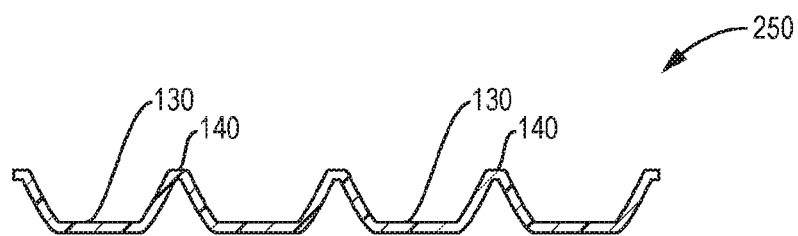
FIG. 2B depicts a cross section view of the textured or embossed pattern of FIG. 1B.

The container is bound by one or more walls, typically made of a flexible film. The walls comprise an inside and outside surface relative to the container. In some embodiments, the container comprises at least one wall that has an internal surface that is not smooth. In other words, the internal surface of at least one wall has a texture. The texture provides a plurality of channels on the surface of the wall, which facilitates fluid (e.g., a liquid or a gas) to pass through the channels. The texture can be any suitable texture such that the texture provides a plurality of channels. For example, the texture can be irregular, random, patterned, non-patterned, symmetrical, non-symmetrical, repeating or non-repeating. The texture may be matte, embossed, grooved, or otherwise formed on the surface of the film. FIGS. 1A-1B illustrate examples of texture that is embossed on a flexible film; FIGS. 2A-2B illustrate cross section views of the textures embossed on the flexible films of FIGS. 1A-1B.

FIG. 1A depicts a textured or embossed pattern having raised features 110 and recessed channels 120 on an interior of a flexible film 100 according to embodiments of the disclosure. As shown, FIG. 1A depicts raised areas 110 and channels 120, wherein the raised areas 110 are shown as squares. It is to be understood that other geometries are possible. For example, circular raised areas, rectangular raised areas, rhomboidal raised areas, etc. Also, in some embodiments, the squares, circles, rhomboids, etc., may be recessed from a surface. In such embodiments, the channels in FIG. 1A would present as raised rails, as discussed below. In the example of FIG. 1A, the texture comprises a repeating pattern of raised squares 110, wherein the spaces between the raised squares form a plurality of channels 120, which are optionally interconnected, through which a fluid, e.g., a biological fluid being processed or a gas during vacuum integrity testing, can pass. The texture can be formed from any shape, not just squares, such as circles or dots, lines or grooves, a weave pattern, or other such shape. Any of the embossing patterns disclosed herein comprise peaks and valleys, i.e., raised areas (e.g., squares) and channels extending between the raised areas. In some exemplary embodiments, the height of the raised areas is approximately 0.06 mm to approximately 0.013 mm. The width of the raised areas may comprise, for example, approximately, 0.05 mm to 0.10 mm. It is to be understood that other sizes and dimensions of embossed areas are within the scope of the present disclosure. It is to be further understood that the embossed pattern in any film may be the same as or different from other embossed patterns irrespective of the size of the bag to be tested using embodiments of the methods disclosed herein. FIG. 2A depicts a cross section view 150 of the textured or embossed pattern of embodiments of FIG. 1A. FIG. 2A more clearly indicates that the cross section 150 of the flexible film 100 of FIG. 1A comprises raised features 110, displayed as squares, and recessed areas 120, wherein the raised features 110 are disposed on the flexible film 100 on an interior of a bag or biocontainer.

FIG. 1B depicts a textured or embossed pattern having recessed features 130 and raised channels 140 on an interior of a flexible film 200 according to embodiments of the disclosure. The embodiments of FIG. 1B are substantially the mirror of the embodiments of FIG. 1A. FIG. 2B depicts a cross section view 250 of the textured or embossed pattern of embodiments of FIG. 1B. FIG. 2B more clearly indicates that the cross section 250 of the flexible film 200 of FIG. 1B comprises raised rails 140 and recessed areas 130, displayed as squares, wherein the raised rails 140 are disposed on the flexible film 200 on an interior of a bag or biocontainer.

In some embodiments, the container comprises at least two opposing flexible walls. The internal surface of each of the two opposing walls may each, or individually, comprise a plurality of channels on said walls. In at least one embodiment, the internal surface of all walls of the container are textured and comprise a plurality of channels. In some embodiments, the texture on opposing walls are non-interlocking with each other, such that when the opposing walls are adjacent to each other, the channels are not obscured or blocked by the texture on the opposing wall.

In performing the vacuum integrity test(s), the plurality of channels formed by the texture allows for the contents of the flexible container to be evacuated, such as by vacuum suction. In some embodiments, the flexible container undergoes a vacuum until a negative pressure is reached. For example, from approximately −1 (negative) PSI to approximately −14 (negative) PSI. Once the predetermined negative pressure is attained, the air flow is monitored using a mass flow meter. A high air flow, such as 20% or greater air flow, depending on the air pressure during testing, indicates the presence of a defect. In exemplary embodiments, 20% greater air flow can be achieved even, for example, for defects as small as two to five microns in size. Air flow can be monitored and compared to a suitable control, such as an air-tight non-leaking container, and/or a container with a calibrated size orifice. Also, one a bag is evacuated, a loss of vacuum can only be the result of a defect or leak in the bag, i.e., vacuum decay, a state or condition of a loss of vacuum. In some exemplary embodiments, testing may occur from a range of approximately −5 (negative) PSI to approximately −7 (negative) PSI.

Figure 9:
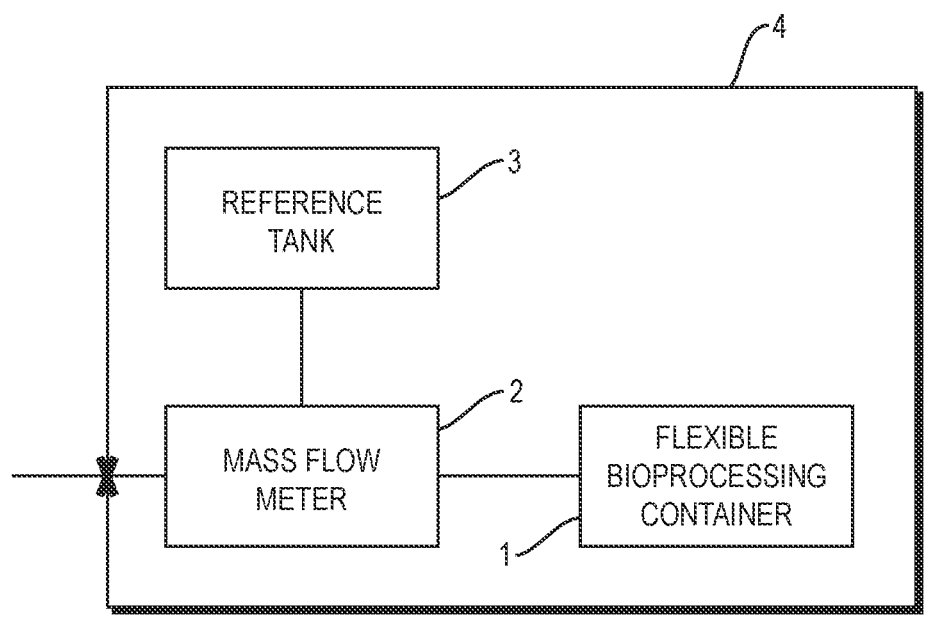
FIG. 9 is a schematic diagram outlining an exemplary integrity testing system 4, according to some embodiments of the disclosure.

FIG. 9 is a schematic diagram outlining an exemplary integrity testing system 4, according to some embodiments of the disclosure. Generally, during the test the flexible container 1 is in direct communication with a rigid steel reference tank 3. Both the tank 3 and flexible container 1 are evacuated of air. Once the evacuation is complete, the system 4 is sealed, and a mass flow meter 2 situated between the reference tank 3 and the flexible senses any air flow from the container to 1 the reference tank 3.

As described herein, the size of a defect, or a leak, detected comprises a range of approximately 1-250 microns, and more typically approximately 2-10 microns.

In some embodiments, the mass flow is tested for approximately 10 minutes or less, in some embodiments, approximately 2 minutes or less, more typically, approximately 20-30 seconds.

Figure 4:
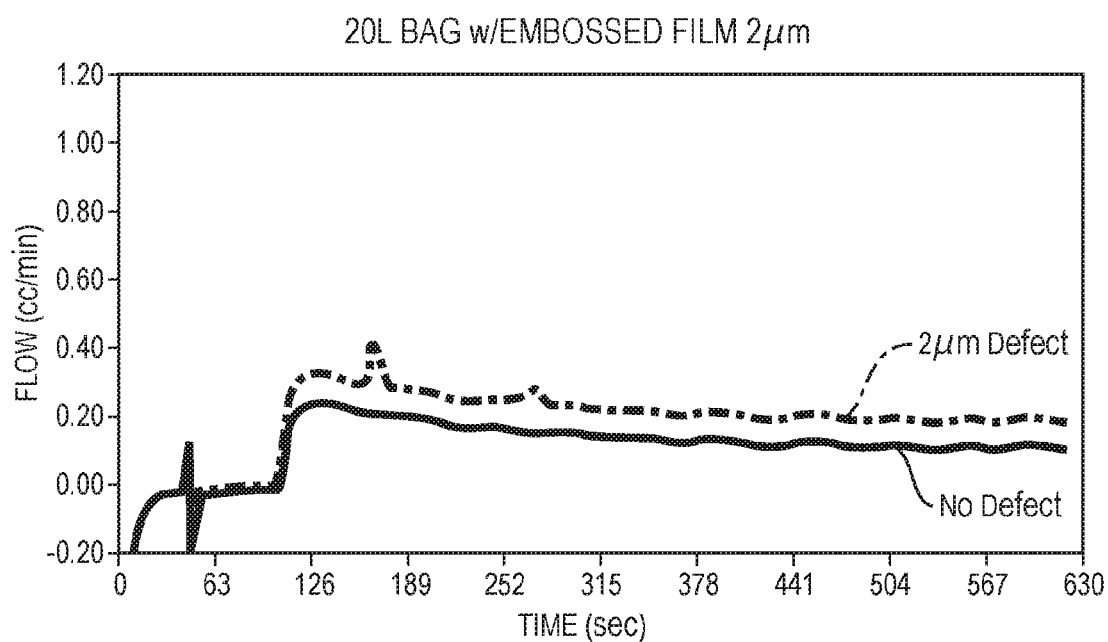
FIG. 4 is a graph comparing integrity test results of a small (20 L) embossed bag with a 2 μm sized defect, compared to the same bag having no defect.
Figure 5:
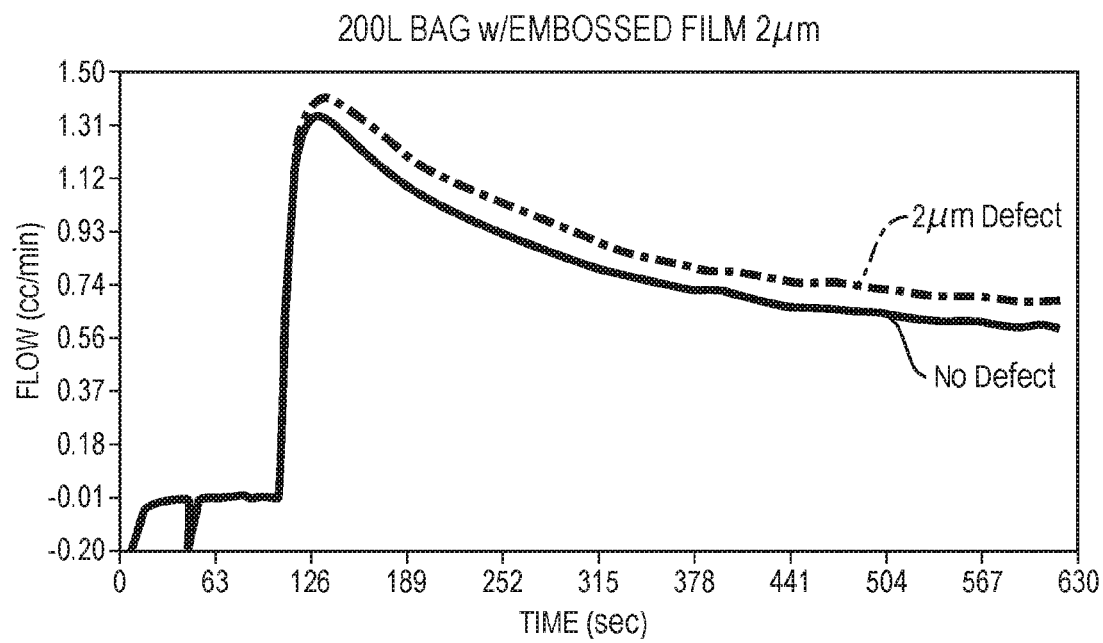
FIG. 5 is a graph comparing integrity test results of a larger (200 L) bag with a 2 μm defect, compared to the same bag having no defect.
Figure 6:
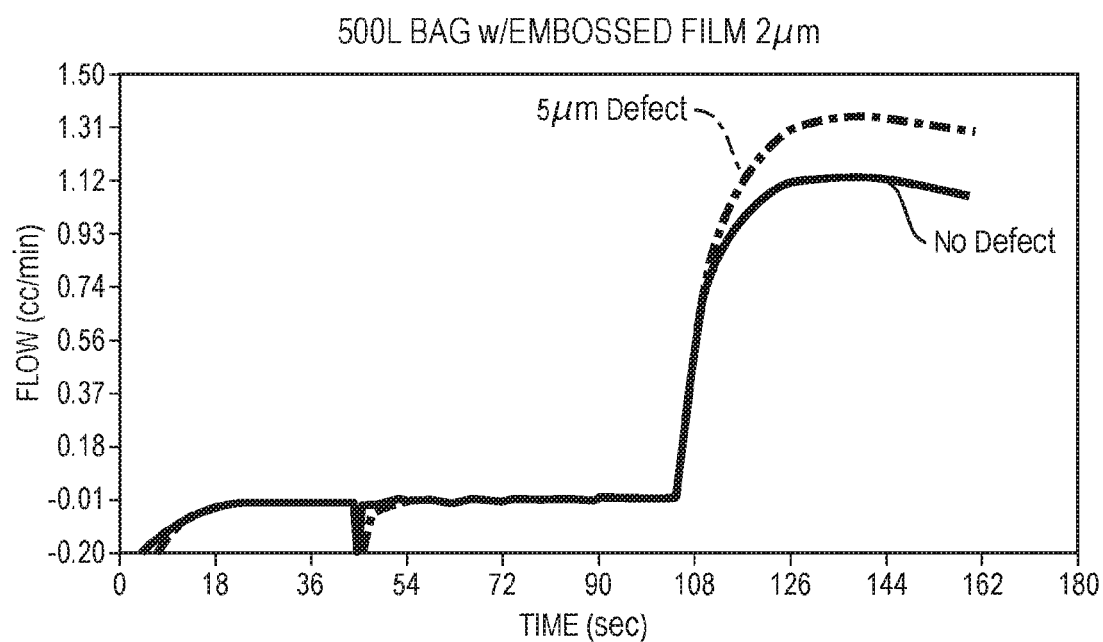
FIG. 6 is a graph comparing integrity test results of a large (500 L) bag with a 5 μm defect, compared to the same bag having no defect.

FIG. 3 shows a graph comparing the vacuum integrity test on a textured (embossed) film bag with a standard non-textured surface bag. In this embodiment, a 20-foot long (which may be, for example, 5 inches wide), 20-liter bag was integrity tested with artificially introduced defects of varying sizes. Defects were introduced as either laser-drilled holes of 100 microns and 50 microns ("in film") or as a 30 micron hole in a fitting attached to the bag ("in tube"). An increase in flow rate was detected in less than 30 seconds for defects in bags with an embossed film, whether on the bag or on the fitting. The relationship between the container and the test sensitivity is indicated in FIGS. 4-6.

Figure 7:
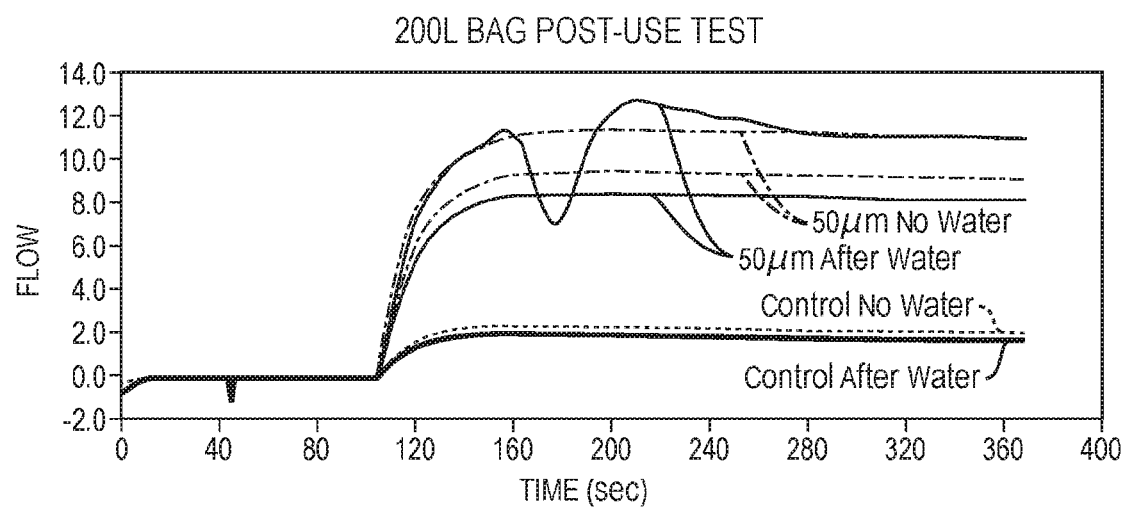
FIG. 7 is a graph comparing integrity test results of a 200-liter bag after use (filled with water and emptied) with a 50 μm defect, compared to a 200-liter bag with a 50 μm defect before use (not filled with water), a 200-liter bag having a defect both before and after use.

FIG. 7 confirms that the vacuum integrity test can be performed post-use of the bag. For example, a container can be filled with fluid (such as for mixing, bioprocessing, etc.). Following use, confirmation of the integrity of the container may be desired. Typically, once the container is drained, some residual fluid may remain. This residual fluid should be prevented from entering the mass flow meter. As such, the residual fluid can be evacuated under vacuum into a water trap before conducting the vacuum integrity test. By inclusion of valves in the system, contents from the container can be first diverted through the water trap before commencing the vacuum integrity test. Filters are further optionally included in the lines.

Figure 8:
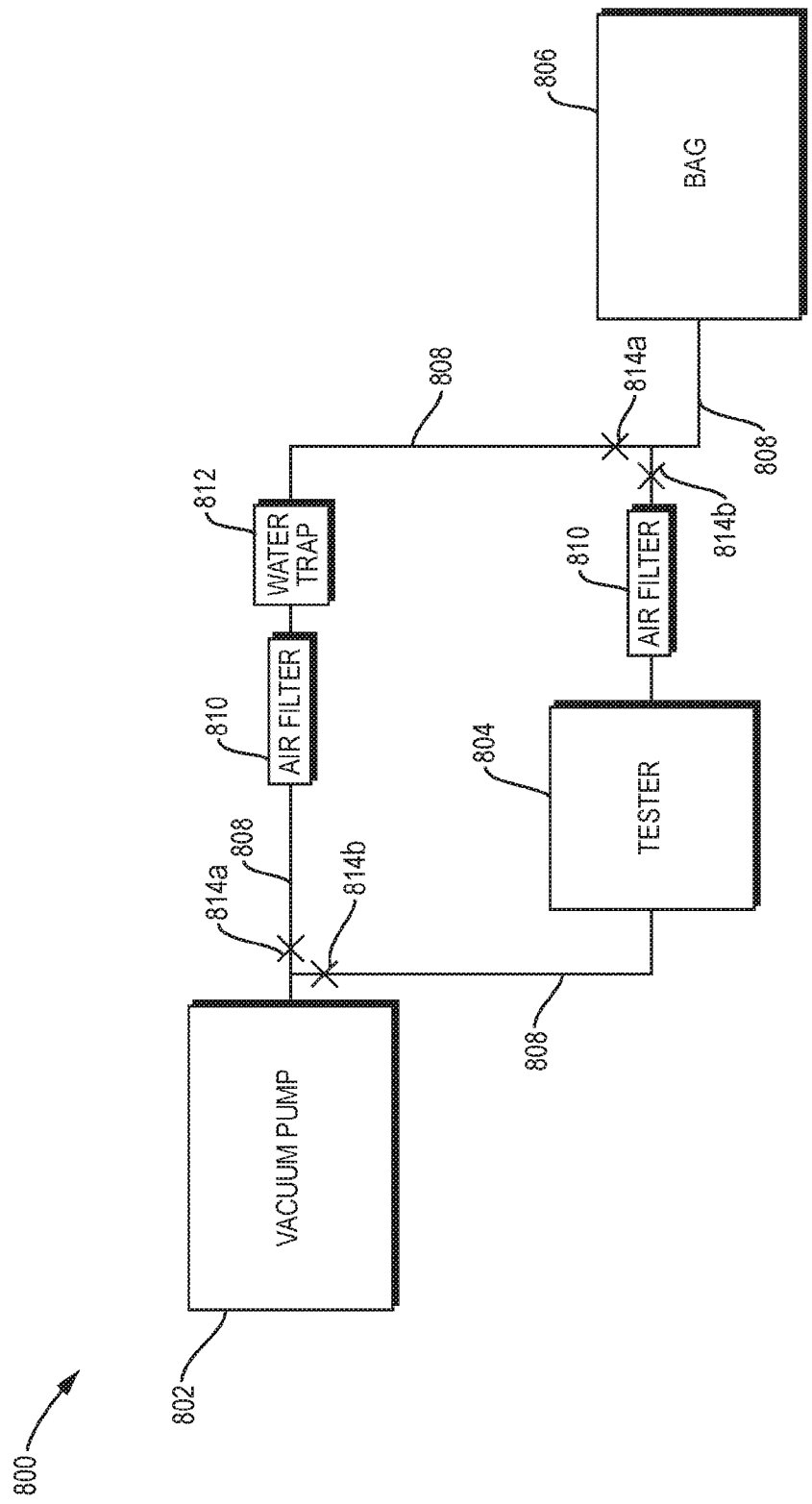
FIG. 8 is a schematic diagram outlining an exemplary integrity testing system of some embodiments of the disclosure.

FIG. 8 is a schematic diagram outlining an exemplary integrity testing system 800 of some embodiments of the disclosure. The system may be used to vacuum integrity test a container, e.g., a biocontainer or a bag, after use, such as after fluid has been handled in the container and drained. Residual fluid left in the container may be captured in the water trap before conducting the vacuum integrity test. The water trap system is an optional component and may be omitted if no or little fluid is present in the container being tested.

The integrity testing system 800 comprises a vacuum pump 802, a tester 804, and a bag 806 to be tested, for example, a bag or biocontainer having an embossed film, as described in greater detail above. The vacuum pump 802, the tester 804, and the bag 806 are connected via conduits 808. The integrity testing system 800 may further comprise one or more air filters 810. The integrity testing system 800 may also further comprise one or more water traps 812, according to some embodiments of the disclosure. The integrity testing system 800 may further comprise one or more valves 814, for opening and closing as appropriate. For example, the valves 814b may be closed in conduits 808 adjacent to the tester 804. While the valves 814a are open, pulling a vacuum permits water to flow and be trapped by a water trap 812. Subsequently, the valves 814b are opened and the valves 814a closed, so that the bag 806 may be tested in a substantially liquid, e.g., water-free environment. The integrity system 800 may be used before or after the bag 806 is used to process, for example, biological liquids. The vacuum pump 802 pulls a vacuum, e.g., from −1 to −14 PSI, from the bag 806, wherein the tester 804 is disposed between the vacuum pump 802 and the bag 806. The tester 804 will indicate a flow of air or, alternatively, a loss of vacuum, as described above, if a defect is present in the bag 806.

It is to be understood that any of the embodiments of the film(s) to manufacture a container and/or biocontainer, as described herein, may comprise a single layer film or a multilayer film. It is to be further understood that whether a single layer film or a multilayer film, either may be textured or embossed. It is further to be understood that the internal contact layer of any film would be textured or embossed. It is further to be understood that any embodiments of the container, biocontainer, or film can be textured or embossed as is known to those in the art. For example, the single layer film or the multilayer film can be embossed during an initial extrusion, after extrusion, e.g., a secondary operation, or can be embossed after all layers, i.e., for a multilayer film, are laminated, calendared, or otherwise adhered together.

The integrity test(s) described herein uses a vacuum and consequently is not limited in the size or shape of the container being tested. Outlets, inlets, ports or other openings in the container or on any attached fittings, can be sealed or closed prior to the vacuum integrity test. The described integrity test can be universally applied to bioprocessing containers and systems and overcomes shortcomings of standard inflation-based integrity tests.

At least some testing methods according to embodiments of the disclosure comprises evacuating air from a container to a negative atmospheric pressure, the container being a collapsible, flexible container, and comprising at least two opposing flexible walls, wherein a surface of at least one of the walls internal to the container comprises a plurality of channels on said at least one wall and, monitoring mass flow (or the loss of vacuum) so as to determine the integrity of the container, i.e., the presence or absence of a defect.

At least some testing methods of detecting a 2 micron or larger defect in a collapsible, flexible bioprocessing container, the method comprise providing a collapsible, flexible bioprocessing container, the container comprising at least two opposing flexible walls, wherein the surface of the walls internal to the container comprise a plurality of channels on said walls; evacuating air from the container to a negative atmospheric pressure; and monitoring mass flow, wherein an increase in mass flow indicates the presence of a defect.

Any of the testing methods according to the disclosure may comprise wherein the negative atmospheric pressure is between about −1 PSI to −14 PSI. Any of the testing methods according to the disclosure may comprise wherein the surface of the at least one wall is a matte surface or an embossed surface. Also, any of the preceding methods may comprise wherein the collapsible, flexible container(s) is pre-folded.

EXAMPLES

Tests were conducted to compare the vacuum integrity test on traditional, flat or non-embossed film containers versus embossed film containers. As shown in FIG. 3, non-embossed film with or without a 30 μm defect was similar to the test result of embossed film with no defect (control). In contrast, the embossed film with a 30 μm defect was readily distinguishable from control within seconds of starting the test (start time point at approximately 98 seconds). By 102 seconds (e.g., less than 4 seconds of test time), the defect in the embossed film 20 L container was conclusively identified.

FIG. 4 demonstrates that the vacuum integrity test is highly sensitive, finding a single 2 μm hole in a 20-liter bag manufactured using an embossed film, as described herein. The flow of air, in cubic centimeters per minute, is significantly higher, and easily detectable, for the bag having a defect as small as 2 microns.

FIGS. 5 and 6 demonstrate that the increasing the size of the test container to 200-liters and even 500-liters nonetheless positively identifies defects as small as 2 microns in embossed film containers. Note that the initial increase in mass flow results from opening the valve to the instrument.

FIG. 7 demonstrates that the vacuum integrity test positively identifies defects in embossed film containers post-use. As described above, it may be desirable to test a flexible container after use to confirm integrity. This test confirms that 50 μm defects were positively identified in embossed film bags pre- and post-use as compared to an embossed film control without a defect pre- and post-use.

The present disclosure is not to be limited in scope by the specific embodiments described herein. Indeed, other various embodiments of and modifications to the present disclosure, apparent to in addition those of to those described herein, ordinary skill in the art will from be the foregoing description and accompanying drawings. Therefore, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be contemplated in view of the full breadth and spirit of the present disclosure as described herein.

What is claimed is:

1. A method for integrity testing a collapsible, flexible bioprocessing container using a system, the method comprising:
    a) providing a collapsible, flexible bioprocessing container, wherein the container comprises at least two opposing flexible walls, wherein the surface of the walls internal to the container comprise a plurality of channels on said walls;
    b) evacuating air from the container and a reference tank connected to the container to a negative atmospheric pressure;
        sealing the system, the system comprising the container, the tank, and a tester between the container and the tank; and
    c) monitoring mass flow of air entering the system using the tester, so as to determine the integrity of the container.

2. The method of claim 1, wherein the plurality of channels are embossed on said walls.

3. The method of claim 1, wherein the surface of the walls are matte surfaces.

4. The method of claim 1, wherein the collapsible, flexible bioprocessing container is pre-folded.

5. The method of claim 1, wherein the collapsible, flexible bioprocessing container further comprises fittings, tubing, connectors, and a combination thereof.

6. The method of claim 1, wherein the negative atmospheric pressure is between −1 psi to −14 psi.

7. A method of detecting a 2 micron or larger defect in a collapsible, flexible bioprocessing container, the method comprising:
    a) providing a collapsible, flexible bioprocessing container, the container comprising at least two opposing flexible walls, wherein the surface of the walls internal to the container comprise a plurality of channels on said walls;
    b) evacuating air from the container and a reference tank connected to the container to a negative atmospheric pressure;
    c) sealing the system, the system comprising the container, the tank, and a tester between the container and the tank; and
    d) monitoring mass flow of air entering the system using the tester, wherein an increase in mass flow indicates the presence of a defect.

8. The method of claim 7, wherein the plurality of channels are embossed on said walls.

9. The method of claim 7, wherein the surface of the walls are matte surfaces.

10. The method of claim 7, wherein the collapsible, flexible bioprocessing container is pre-folded.

11. The method of claim 7, wherein the container further comprises fittings, tubing, connectors, and a combination thereof.

12. The method of claim 7, wherein the negative atmospheric pressure is between −1 psi to −14 psi.

13. The method of claim 8, wherein the surface of the walls are matte surfaces.

* * * * *